United States Patent
Renello

(10) Patent No.: US 6,172,051 B1
(45) Date of Patent: Jan. 9, 2001

(54) ENHANCED TERMITICIDE AND METHOD FOR TREATING TERMITES

(76) Inventor: Leo A Renello, 8540 E. McDowell, Lot 60, Mesa, AZ (US) 85207

(*) Notice: Under 35 U.S.C. 154(b), the term of this patent shall be extended for 0 days.

(21) Appl. No.: 08/832,068

(22) Filed: Apr. 2, 1997

(51) Int. Cl.⁷ .................... A01N 57/00; A01N 25/00
(52) U.S. Cl. .................................. 514/89; 424/84
(58) Field of Search .................... 514/89; 414/84

(56) References Cited

U.S. PATENT DOCUMENTS

| | | | |
|---|---|---|---|
| 3,858,346 | 1/1975 | Bailey | 43/124 |
| 4,310,520 | * 1/1982 | Narazaki | 424/200 |
| 4,582,901 | 4/1986 | Prestwich | 536/83 |
| 4,849,415 | * 7/1989 | Zweigle | 514/89 |
| 5,564,222 | 10/1996 | Brody | 43/124 |
| 5,573,760 | 11/1996 | Thorne et al. | 424/84 |

OTHER PUBLICATIONS

Homeowner's Guide to the new Firstline Termite Bait Station, FMC Corporation Oct. 1996.
Specimen Label for Firstline Termite Bait Station, FMC Corporation Apr. 1996.

* cited by examiner

*Primary Examiner*—Allen J. Robinson
(74) *Attorney, Agent, or Firm*—Joseph W. Mott

(57) ABSTRACT

An improved termiticidal combination is formed by adding a liquid cellulose source to a standard liquid termiticide. The cellulose source may be a water soluble polyester such as a cellulose ether like methyl cellulose. The cellulose in the combination functions as termite bait, thereby enhancing the effectiveness of the poison, even at lower concentrations, by inducing termites to ingest poisoned cellulose and return with it to share it with the colony. The liquid form allows the combination to be applied with a standard power sprayer, and permits laying of a continuous barrier or curtain as well as injection spraying into walls of structures.

15 Claims, No Drawings

ENHANCED TERMITICIDE AND METHOD FOR TREATING TERMITES

FIELD OF THE INVENTION

The invention relates to the field of pesticides in general and more specifically to termiticides.

BACKGROUND OF THE INVENTION

Subterranean termites present a serious threat to structures, and particularly residential structures, throughout most of the United States and in many parts of the world. One of the most widely used techniques to combat termite infestation is the application of chemical agents to the ground under and around the structure. In a typical preconstruction treatment situation, a liquid form termiticide is sprayed at specified concentrations and volumes directly onto the compacted soil immediately before the concrete slab is poured, creating a horizontal barrier between any subterranean nests and the underside of the slab. Additional barriers are created in by boring holes into the soil at specified intervals (often 18 inches) or by digging trenches around the structure and spraying termiticide into the openings as well as Mixing termiticide with the backfill soil. If treatment is required to control active infestation that occurs after construction, techniques include drilling holes in infested walls and injecting liquid or powdered termiticides between the walls, boring holes in the floor slab at spaced intervals and injecting liquid termiticides into the soil, and trenching around the base of the structure and applying termiticides as in pretreatment.

In the past conventional insecticides such as the chlorinated hydrocarbons known as chlordane, DDT, aldrin, dieldrin and BHC could be effectively used to poison the soil so that transiting termites would be killed. These chemicals also remained effective in the ground for many years. Unfortunately, their effectiveness as poisoning agents extended beyond the targeted pests, and environmental concerns have resulted in prohibition of the use of any of these agents for termite treatment. Chlordane was the last such chemical available for either home or professional use, and that was banned by the United States Environmental Protection Agency in 1987.

The pest control industry has been forced to adopt a less potent class of chemical poisons for termite pre-treatment and infestation interdiction. Currently approved by the Environmental Protection Agency are chlorpyrifos (sold under the name DURSBAN TC), cypermethrin (sold as DEMON TC), fenvalerate (sold as TRIBUTE), and permethrin (sold as DRAGNET and as PRELUDE). These chemicals are generally applied in the same manner as their predecessor chlorinated hydrocarbons, namely, spraying beneath a slab or other foundation to form a horizontal barrier and injection through holes or a trench to form a vertical barrier or "curtain" through which terminates cannot penetrate without being killed. They are also used for infestation control. Unfortunately, the very characteristics that make them acceptable from an environmental standpoint (low toxicity and eventual degrading into non-toxic components) render them less effective in long term termite control.

One of the most common termiticides, and the only one available to consumers who are not licensed pest control operators, is chlorpyrifos, an organophosphate that is available in emulsifiable concentrate, dust, flowable, pellet, spray, granular and wettable powder formulations. The chemical adsorbs well to soil particles, is not readily soluble in water, and has a half life of 2 weeks to a year, but most commonly 60 to 120 days. Chlorpyrifos acts as a cholinesterase inhibitor, interfering with the proper working of the nervous system. It works as a contact poison, but also as a stomach poison. A conventional termite barrier laid down by spraying chlorpyrifos is expected to kill termites that pass through it, and to generate secondary kills in the nest when the carcasses of poisoned termites are carried to the nest and cannibalized. The half life virtually assures that the efficacy of the chemical will end before that of the structure.

To enhance the effectiveness of termiticidal compounds, both before and after the banning of chlorinated hydrocarbons, the chemicals were combined into termite "baits" consisting of the poison and an attractive termite food, namely, some form of cellulose. The objective is to induce the termites to ingest the poisoned food and return with it to the nest, where food is normally regurgitated and shared with the rest of the colony. Two early examples are U.S. Pat. No. 3,858,346 (Bailey) and U.S. Pat. No. 4,582,901 (Prestwich). Bailey disclosed impregnation of building timbers with hexachlorocyclopentadiene dimer in an organic solvent such as benzene or carbon tetrachloride as the termiticide, and also spreading bait comprising the same poison added to a termite-attracting carbohydrate carrier such as citrus pulp, sawdust and decaying wood. Prestwich discloses modifying the chemical composition of cellulose to include fluorinated ester moieties. The modified cellulose may be formed into bait blocks or injectable dust for placement in areas to be protected or treated.

In more recent, environmentally safer approaches, U.S. Pat. No. 5,564,222 (Brody) discloses impregnating cellulose items, such as wc, oden or cardboard stakes, balls or pellets with a wa t soluble borate salt. The termites are attracted to and consume the cellulose and the borate salt functions as a slow-acting termiticide. U.S. Pat. No. 5,573,760 (Thorne, et al.) discloses using a termite monitor in the form of a perforated cartridge containing a cellulose-rich composition, water and an exogenous nitrogen source. Once foraging termites encounter the desirable food source, they recruit others, and a tunnel to the device is constructed. This allows early detection of termites near a protected structure, as the bait is a more desirable food than the structure. Once activity is identified, the cartridge can be removed and replaced with a similar cartridge containing the same food composition, but laced with a slow-acting termiticide.

The bait approach as previously implemented has at least two disadvantages. First, there are necessarily gaps between the bait modules, leaving the possibility that termites may simply miss the bait, tunneling between the modules and reaching and infesting the protected structure. Current protection standards require a horizontal barrier and vertical curtain without any gaps. Second, placing of the bait modules, whether spikes, buried balls, pellets or dust, is time consuming, labor intensive and consequently expensive. The closer together the bait modules, the more work and expense involved.

Thus, it is an object of the invention to provide a termite control mixture that includes a poison mixed with a food source that may be, applied uniformly across an area of property. It is a further object to provide a mixture of termiticide and food that may be applied using the same equipment and techniques employed by pest control operators to administer standard termiticidal compounds. It is a further object to distribute the mixture in the ground to form a continuous barrier between subterranean termites and the structure to be protected. It is another object to enhance the effectiveness of a given amount of poison by inducing termites to ingest poisoned food and return with it to the nest, poisoning other termites and the queen. It is yet another object of the invention to afford termite protection and control using a smaller amount of potentially harmful poison than is necessary with standard termiticides.

SUMMARY OF THE INVENTION

The present invention provides a way to continue the easy application of an unbroken termiticide barrier while also taking advantage of the enhanced effectiveness offered by termite baiting techniques. A soluble, polymer form of cellulose, such as methyl cellulose or another of the cellulose ethers, is combined with the standard concentration of an approved liquid termiticide, such as chlorpyrifos. The viscosity of the cellulose ether is controllable, and may be set so that the mixture can be broadcast with the conventional pressure spray applicators used in the pest control industry. Thus, the identical termiticide barrier formation procedures may be used to apply the same concentrations of approved chemicals as before, but mixed with a source of food sought by termites. Termites encountering the barrier will ingest the poisoned cellulose and return to the colony to share the toxic food.

DETAILED DESCRIPTION OF THE INVENTION

The invention is a liquid, sprayable mixture of termiticide and a cellulose source, capable of being applied to soil as a barrier in the same manner as conventional termiticides are currently broadcast. The mixture's viscosity must allow it to flow through a conventional pressure spray applicator, and it must penetrate and hold in soil to a depth of about 1–2 inches (2.5–5 cm), approximately the same as liquid termiticides in prescribed concentrations. Commercially available, EPA-approved termiticides form the poison component of the mixture. Some such termiticides are available only to licensed pest control operators, while others may be available for home use.

The liquid cellulose component of the mixture may be readily obtained from commercial sources. Ingestible, nearly pure cellulose is available in water soluble polymer form as a cellulose ether. One of the cellulose ethers, methyl cellulose, has been widely used in foods, pharmaceuticals, personal care products, and coatings for over 50 years. Methyl cellulose is available in varying grades of purity up to those approved for human consumption and in a wide range of viscosities.

Other forms of cellulose, or cellulose ethers, for example CMC, HEC, HPC, HEMC, HPMC, ethyl cellulose or HEEC, may bu used in the invention. The important characteristics are that the mixture include cellulose, the primary food source for termites, and that the mixture of termiticide and cellulose have a liquid form (which may include colloidal or other suspensions) that can be dispensed through a sprayer or applicator similar to those used in the pest control industry. In like manner, the termiticide component may be any effective termite poison dispensable as a liquid, including the now-banned chlorinated hydrocarbons.

Although the scope of the invention encompasses various combinations of termiticides and cellulose, the experimentation performed and the detailed description below is focused on a particular formulation of the invention, namely, a mixture of methyl cellulose and a liquid chlorpyrifos. Methyl cellulose is widely available, particularly fr Dow Chemical Company. Chlorpyrifos, a broad spectrum insecticide, is sold under the names DURSBAN, BRODAN, DETMOL UA, ERADEX, LORSBAN, PIRIDANE, STIPEND and CHLORPYRIFOS PRO. The experiments used CHLORPYRIFOS PRO, available to licensed pest control operators. The methyl cellulose was a form commonly used in the motion picture industry for creating special-effects (particularly the appearance of bleeding wounds) and as a non-toxic adhesive or fixative. When purchased as a liquid it is known as "studio paste" and when purchased for the latter use, it is available in a powder known as "cellulose adhesive."

EXAMPLE 1

The initial testing was designed to confirm that the mixture would be effective, i.e., that termites would actually eat the poison-laced cellulose. Four separate experiments were performed, each using approximately 200 live Formosa termites obtained from the United States Department of Agriculture, U.S. Forestry Service, Tucson Office. A termite tank was set up in a 10 gallon aquarium with a plastic center divider situated so that termites could circulate around the divider.

On one side of the divider, approximately 200 live termites were placed, along with a 2" (5 cm) cover of untreated soil. On the other side, a 2" (5 cm) cover of soil treated with the experimental mixture was set. The chlorpyrifos concentration was maintained constant at 64 oz. (1900 ml) in 50 gallons (189 l) of water. In successive trials, the concentration of cellulose in the treated soil, as determined in a laboratory by a standard Total Organic Carbon test, was varied. Observations of the effect on the live termite sample were recorded, as summarized in Table 1. In each case, termites were observed feeding on the treated soil within 24 hours after the test started. The results showed that the cellose in fact attracted termite activity once the food source was discovered by foragers, and the termites perished from the poison within a few days. Higher concentrations of cellulose accelerated the kill rate.

TABLE 1

Percentage of Termites Killed Over Time

| Cellulose in Treated Soil | Days from Start | | | | | | | | |
| --- | --- | --- | --- | --- | --- | --- | --- | --- | --- |
| | 2 | 3 | 4 | 5 | 6 | 7 | 8 | 9 | 10 |
| 3600 ppm | | 25% | 55% | 75% | | | 85% | | 100% |
| 7200 ppm | 40% | 75% | 95% | 100% | | | | | |
| 10,000 ppm | 85% | 95% | 100% | | | | | | |
| 5,435 ppm | 35% | 60% | 80% | 95% | | | 100% | | |

EXAMPLE 2

A test was designed to confirm that the inventive mixture penetrates the soil to an appropriate depth and leaves a cellulose-rich termiticide barrier. A 2 acre test site was set up in an area having some dry, caleche-like soil, some sandy loam soil, and some typical Arizona high-organic soil. A few test sites were compacted to form a preconstruction base course for concrete slab construction.

For each trial, a 30 ft by 30 ft (10 m×10 m) section of ground was selected. A half-inch (1.25 cm) diameter tubular soil probe was plunged to a depth of about one inch (2.5 cm) in 14 to 16 sample locations spread throughout the test section. Each pretreatment sample was aerated in a bucket, then transferred to a sealable plastic sample bag. The selected a area was then treated with a sample mixture at controlled concentrations; the mixture was sprayed evenly across the area at a pressure below 45 psi using a standard professional pest control operator setup including a 1 horsepower pump, 5 horsepower motor and a raindrop tip applicator. The soil was allowed to dry, usually overnight, and then was sampled with the soil probe in 14 to 16 locations, generally near the holes where pre-treatment examples had been extracted. Samples were aerated as before and sealed in plastic bags for transport to the laboratory.

For each test, the pre-treatment and post-treatment aggregated samples were subjected to a Total Organic Carbon analysis to ascertain the post-application increase in organic carbon material, from which the amount of residual cellulose in parts per million can be derived. Similar sampling and analytical testing was undertaken at residences treated for infestation as described in more detail below. The results of the testing are set out in Table 2. It should be noted that in about 30% of the samples (not shown in the table), the high organic content of the untreated soil rendered the Total Organic Carbon test ineffective in detecting any post-treatment residual cellulose.

TABLE 2

| Sample | Termiticide | Amount Termiticide[1] | Amount Cellulose[2] | Amount Water | Residual Cellulose |
| --- | --- | --- | --- | --- | --- |
| Test Area Treatments | | | | | |
| 223 | Chlorpyrifos | 1792 oz (52990 ml) | 7 lb (3.175 kg) | 900 gal (3406 l) | 3300 ppm |
| 775 | Dursban | 64 oz (1900 ml) | 550 cc | 30 gal (114 l) | 2600 ppm |
| 779 | Dragnet | 64 oz (1900 ml) | 550 cc | 30 gal (114 l) | 3260 ppm |
| 783 | Demon | 64 oz (1900 ml) | 550 cc | 30 gal (114 l) | 4130 ppm |
| 787 | Tribute | 64 oz (1900 ml) | 550 cc | 30 gal (114 l) | 5200 ppm |
| Residence Treatments | | | | | |
| 835 | Chlorpyrifos | 96 oz (2840 ml) | 687 cc | 100 gal (378 l) | 391 ppm |
| 773 | Chlorpyrifos | 64 oz (1900 ml) | 825 cc | 30 gal (114 l) | 5870 ppm |
| 781 | Chlorpyrifos | 96 oz (2840 ml) | 620 cc | 100 gal (378 l) | 3260 ppm |
| 785 | Chlorpyrifos | 96 oz (2840 ml) | 756 cc | 60 gal (227 l) | 650 ppm |
| 15 | Chlorpyrifos | 64 oz (1900 ml) | 620 cc | 100 gal (378 l) | 7200 ppm |

Notes:
1. Liquid ounces
2. Dry volume of methyl cellulose powder (except Sample 223)

It may readily be seen that the in-ground concentrations of 3300 to 7200 ppm of cellulose are achievable using reasonable amounts of methyl cellulose in the mixture. The termiticide barrier concentration was assumed to be the same as industry standards inasmuch as the chlorpyrifos concentration of the mixture was the same as a standard application, with the addition of methyl cellulose being the only change. It was observed during the spraying process that the cellulose in the samples tended to precipitate making it necessary to slowly agitate the mixture so it remains in solution. Because of the range of viscosity control, it is expected that cellulose components without this problem may be utilized, but in any event the agitation is easily accomplished, either with a mechanical agitator or by, for example, directing the pressurized return flow from the pump to the tank through a tube with spaced, horizontally-facing holes at the bottom of the tank.

EXAMPLE 3

Field trials in the control of active termite infestation were undertaken at 9 locations. These were residences that had been pretreated using standard termite prevention procedures from 2 to 10 years previously and were now reporting infestation. Live infestation was confirmed at each site before the trial was undertaken. Industry standard remedial termite control applications were performed at each residence, with the specific treatment depending upon the observed nature of the infestation. For example, interior and exterior walls with visible termite activity were drilled and a mixture was sprayed beneath the structure. For each residence a 4 inch (10 cm) to 6 inch (15 cm) trench was dug in the ground along the infested walls, sprayed, backfilled with sprayed soil and sprayed on the surface. At some locations, the termiticide applied was the standard recommended concentration for termite control treatments, while in others the termiticide concentration was cut in half; all had methyl cellulose added to the applicator tank. The residences were inspected generally 2 to 4 weeks later to ascertain whether activity continued. As shown in Table 3, in each case all signs of live infestation had ceased by the time of reinspection.

TABLE 3

| Location No./ Treatment | Treatment Date | Termiticide[1] | Cellulose[2] | Water | Pressure[3] | Return Date |
| --- | --- | --- | --- | --- | --- | --- |
| 1 E Wall Drilled | 12/30/96 | 64 oz (1900 ml) | 1032 cc | 100 gal (378 l) | 20 psi | 1/15 |
| 2 Bedrm N&W Walls Drilled | 1/6/97 | 64 oz (1900 ml) | 860 cc | 50 gal (189 l) | 25 psi | 1/17 |

TABLE 3-continued

| Location No./ Treatment | Treatment Date | Termiticide[1] | Cellulose[2] | Water | Pressure[3] | Return Date |
|---|---|---|---|---|---|---|
| 3 Garage Wall Drilled | 1/9/97 | 96 oz (2840 ml) | 825 cc | 50 gal (189 l) | 20 psi | 1/17 |
| 4 N&E Walls Drilled | 1/13/97 | 96 oz (2840 ml) | 757 cc | 60 gal (227 l) | 20 psi | 2/19 |
| 5 E Back Wall | 1/13/97 | 64 oz (1900 ml) | 825 cc | 30 gal (114 l) | 20 psi | 2/19 |
| 6 All Exterior Walls Except Garage | 1/14/97 | 128 oz (3785 ml) | 620 cc | 100 gal (378 l) | 20 psi | 3/14 |
| 7 All Exterior Walls | 1/14/97 | 96 oz (2840 ml) | 688 cc | 100 gal (378 l) | 20 psi | 3/14 |
| 8 E Wall/Garage | 1/17/97 | 96 oz (2840 ml) | 757 cc | 100 gal (378 l) | 20 psi | |
| 9 SE Bedrm Wall | 1/17/97 | 96 oz (2840 ml) | 757 cc | 100 gal (378 l) | 20 psi | 3/20 |

Notes:
1. Termiticide in liquid measure of full-strength CHLORPYRIFOS PRO
2. Cellulose in dry volume of methyl cellulose powder
3. 20 psi = 13790 newtons per square meter; 25 psi = 17237 newtons per square meter The inventive mixture is thus shown to be particularly effective in control of active infestation. By combining the characteristics of a contact-kill barrier and a bait that is carried back to the colony, the invention provides an effective control procedure that does not required the full concentrations of potentially harmful poisons usually employed for such purpose.

Although the present invention has been described in considerable detail with reference to certain preferred versions thereof, other versions are possible. For example, a variety of liquid cellulose sources and termite poisons may be employed in the mixture. Some forms of cellulose source, particularly methyl cellulose, may be sufficiently soluble so that the invention mixture may be prepared and stored in containers to be mixed later with water before use. Other forms, such as the powdered form used in the examples, is better kept separate from the termiticide concentrate and added to the applicator tank immediately before broadcasting the mixture. Therefore, the spirit and scope of the appended claims should not be limited to the description of the preferred versions contained herein.

What is claimed is:

1. A method of pretreating soil beneath a foundation of a future structure so as to protect the structure against termite infestation comprising the steps of preparing a standard termiticide composition by adding chlorpyrifos poison to a prescribed volume of water to achieve a concentration of at least about one-half gallon of poison in 100 gallons of water, adding a cellulose source which when combined with the termiticide composition forms an enhanced liquid composition having a viscosity low enough to permit flow through a pump sprayer, and spraying the enhanced composition on an area of soil beneath and around a location where the foundation is to be placed so as to form a continuous barrier between the future structure and any subterranean termites in the vicinity.

2. The method of claim 1 wherein the cellulose source is a liquid form of a cellulose ether.

3. The method of claim 1 wherein the cellulose source is a powdered or granulated form of a cellulose ether.

4. The method of claim 1 wherein the cellulose source is a liquid form of methyl cellulose.

5. The method of claim 1 wherein the cellulose source is a powdered or granulated form of methyl cellulose.

6. The method of claim 5 wherein about 5 to 30 cc of powdered methylcellulose is added per gallon of water in the liquid.

7. The method of claim 6 wherein the concentration of chlopyrifos is about one-half gallon of poison in 100 gallons of water to about one and one-half gallons of poison in 100 gallons of water.

8. The method of any one of claims 1 through 7 including the further step of agitating the enhanced composition so as to maintain a liquid state with a viscosity appropriate for use with a sprayer.

9. A method of treating live termite infestation of a structure comprising the steps of preparing a standard termiticide composition by adding chlorpyrifos poison to a prescribed volume of water to achieve a concentration of at least about one-half gallon of poison in 100 gallons of water, adding a cellulose source that when combined with the termiticide composition forms an enhanced liquid composition having a viscosity low enough to permit flow through a pump sprayer, and spraying the enhanced composition on and near the location where any live infestation is observed.

10. The method of claim 9 wherein the cellulose source is a liquid form of cellulose ether.

11. The method of claim 9 wherein the cellulose source is a powdered or granulated form of a cellulose ether.

12. The method of claim 9 wherein the cellulose source is a liquid form of methylcellulose.

13. The method of claim 9 wherein the cellulose source is a powdered or granulated form of methylcellulose.

14. The method of claim 9 wherein about 5 to 30 cc of powdered methylcellulose is added per gallon of water in the liquid.

15. The method of claim 14 wherein the chlorpyrifos is added to yield a poison concentration of about one-half gallon of poison in 100 gallons of water to about one and one-half gallons of poison in 100 gallons of water.

* * * * *